United States Patent [19]
Douglas et al.

[11] Patent Number: 6,054,709
[45] Date of Patent: Apr. 25, 2000

[54] METHOD AND APPARATUS FOR DETERMINING THE RATES OF REACTIONS IN LIQUIDS BY MASS SPECTROMETRY

[75] Inventors: Donald J. Douglas; Lars Konermann, both of Vancouver; Bruce Collings, Burnaby, all of Canada

[73] Assignee: The University of British Columbia, Vancouver, Canada

[21] Appl. No.: 08/986,140

[22] Filed: Dec. 5, 1997

[51] Int. Cl.[7] .................................................. H01J 49/04
[52] U.S. Cl. .......................................... 250/288; 250/282
[58] Field of Search .................................... 250/288, 282

[56] References Cited

U.S. PATENT DOCUMENTS

| | | | |
|---|---|---|---|
| 4,861,988 | 8/1989 | Henion et al. | 250/288 |
| 4,935,624 | 6/1990 | Henion et al. | 250/288 |
| 5,009,849 | 4/1991 | Ebner et al. | 250/288 |
| 5,245,186 | 9/1993 | Chait et al. | 250/288 |
| 5,505,832 | 4/1996 | Laukien et al. | 204/452 |
| 5,608,217 | 3/1997 | Franzen et al. | 250/288 |

FOREIGN PATENT DOCUMENTS 0 211 645  2/1987  European Pat. Off. ....... G01N 27/62

OTHER PUBLICATIONS

"An Extended Mass Range Quadrupole for Electrospray Mass Spectrometry", *International Journal of Mass Spectrometry and Ion Processes*, vol. 162, 1997, pp. 121–127 by B. A. Collings and D.J. Douglas.

"Electrospray Mass Spectrometry of Iron Bleomycin: Demonstration That Activated Bleomycin Is a Ferric Peroxide Complex", *J. Am Chem. Soc.*, vol. 116, 1994, pp. 5250–5256 by Joseph W. Sam, Xue–Jun Tang and Jack Peisach.

"Electrospray Mass Spectrometry of Iron Bleomycin II: Investigation of the Reaction of Fe(III)–Bleomycin with Iodosylbenzene", *J. Am. Chem. Soc.*, vol. 117, 1995, pp. 1012–1018 by Joseph W. Sam, Xue–Jun Tang, Richard S. Magliozzo, and Jack Peisach.

"New Concepts in Bioorganic Chemistry, Beyond Enzyme Kinetics: Direct Determination of Mechanisms by Stopped–Flow Mass Spectrometry", *Bioorganic & Medical Chemistry*, vol. 5, No. 4, 1997, pp. 641–644 by Dexter B. Northrop and Frank B. Simpson.

"Britton Reverse Transport Kinetics by Bovine Carbonic Anhydrase II", 17th International Congress of Biochemistry and Molecular Biology, Aug. 24–29, 1997, *FASEB Journal*, vol. 11, (g), p. A1021, 1997, by Dexter B. Northrop and Frank B. Simpson.

"Detection and Identification of Transient Enzyme Intermediates Using Rapid Mixing, Pulsed–Flow Electrospray Mass Spectrometry", *Biochemistry*, vol. 36, No. 49, 1997, pp. 15472–15476 by Anthony A. Paiva et al.

E–Mail dated Mar. 30, 1999 from Karen Anderson to Don Douglas.

(List continued on next page.)

*Primary Examiner*—Jack Berman
*Attorney, Agent, or Firm*—Bereskin & Parr

[57] ABSTRACT

A method and apparatus are provided for determining rates and mechanisms of reactions in solution. The method comprises mixing reactants together and then passing the reactants, after mixing, to an electrospray or other ion source. The apparatus is configured so that the reaction time can be determined. This can either be by way of a capillary of known length and volume extending from a reaction tee or other mixing device, so that the reaction time can be determined from the capillary volume and flow rate, and/or by way of a container of fixed volume from which the reactants pass. From the ion source, ions pass into a mass spectrometer, where a mass spectrum is measured. By varying the reaction time, and measuring the different mass spectra, the rate of reaction can be determined.

19 Claims, 8 Drawing Sheets

OTHER PUBLICATIONS

E–Mail dated Jun. 3, 1999 from Don Douglas to Karen Anderson.

E–Mail dated Jun. 8, 1999, from Karen Anderson to Don Douglas.

Carbonell et al, Flow Injection Flame Atomic Spectrometric Determination of Aluminium, Iron, Calcium, Magnesium, Sodium and Potassium in Ceramic Material by On–line Dilution in a Stirred Chamber, 10428 Journal of Analytical Atomic Spectrometry 6 (1991) Apr.

METHOD AND APPARATUS FOR DETERMINING THE RATES OF REACTIONS IN LIQUIDS BY MASS SPECTROMETRY

FIELD OF THE INVENTION

This invention relates to mass spectrometry (MS). This invention more particularly relates to ESI MS (electrospray ionization mass spectrometry) and APCI (Atmospheric Pressure Chemical Ionization) MS.

BACKGROUND OF THE INVENTION

At the present time, there are a wide variety of known mass spectrometers, including quadrupole, magnetic deflection, TOF (time of flight), Fourier transform and other types of mass analyzers.

Various techniques have been developed for ionizing substances of interest in a liquid solution and introducing the ions into a mass analyzer. Older techniques include fast atom bombardment, ion evaporation and thermospray. More recently, the so-called electrospray ionization (ESI) technique has been developed. In this process, liquid is directed through a capillary tube, the end of which is connected to one pole of a high voltage source. The end of the capillary plate is spaced from an orifice plate through which ions travel into the mass analyzer vacuum chamber. The orifice plate is connected to the other pole of the high voltage source, so as to generate an electric field. This causes charged droplets to travel towards the analyzer. Solvent carried by the droplets evaporates, to leave ions of the substances of interest. Typically an ESI source is operated at solvent flow rates around 1–10 $\mu$L/min which requires the use of a pump. Another known ion source is an Atmospheric Pressure Chemical Ionization (APCI) source. For an APCI source, solvent containing analyte is sprayed into a heated tube where it is vaporized. Solvent and analyte are then ionized by a corona discharge at atmospheric pressure.

Older techniques, or even the more modem ESI and APCI techniques, have generally been applied to liquids or samples which are treated as stable, i.e. they are assumed to have a substantially constant composition, which will remain unchanged for at least as long as it takes to process the sample through the sample introduction system and ion source. In other words, no attempt has been made to use this technique to analyze samples where reactions may be occurring in a relatively short time frame, e.g. of the order of seconds, fractions of a second or several milliseconds. Conventional mass spectrometric techniques, including the ESI technique, simply do not permit reactions occurring on such a short time scale to be captured, since they essentially require the sample to be stable, at least while it is held in some supply vessel, before passing through the capillary to the electrospray nozzle.

Attempts have been made to use mass analyzers to capture changes in concentrations of reactants, as reactions or other changes take place. This can be done by observing the decrease of reactant ion intensity or the appearance of product ions in the mass spectra. In some cases reaction intermediates might be observed. However, conventional techniques, outlined below, are relatively crude, and can only measure events taking place on fairly large time scales, for example of the order of minutes or longer.

Thus, one known technique was described by R. Chavez et al. in a presentation at the 44th ASMS Conference on Mass Spectrometry and Allied Topics, Portland, Oreg., in May 1996. This described manual mixing of reactions with aliquots taken at various times. As will be appreciated, this necessarily resulted in time scales of the order of minutes.

A further, manual mixing technique, with mixing carried out in a vessel connected to an ESI MS, was described by E. D. Lee et al. in the *J. Am. Chem. Soc.* 116 5250–5256, 1994. Again, the time scale was relatively large and was of the order of 0.1 to 10 minutes.

A fundamental difficulty with all of these techniques is that they assume that the electrospray apparatus will have a single capillary to which some sort of vessel must be connected to supply the liquid. This necessarily means that the vessel has some sort of distinct holding time, i.e. time in which the liquid takes to pass through the vessel, which limits the minimum time periods for measuring reactions.

Recently, there has been a proposal for providing on-line mixing coupled to an electrospray apparatus. This is described by J. W. Sam et al., *J. Am. Chem. Soc.* 116, 5250–5256, 1994, and J. W. Sam et al., *J. Am. Chem. Soc.* 117, 1012–1018, 1995. In these proposals, the ability to vary the reaction time by adjusting the flow rate is identified. The apparatus relies on a conventional mixing technique, and there is no discussion as to the effect of the length of the electrospray capillary on reaction times. As such, this provides a so-called mixing chamber, with a relatively large volume of 5 $\mu$L. Consequently, the apparatus only enables a relatively large time scale of the order of a few seconds to a few minutes to be used.

Moreover, the earlier techniques relying on manual mixing are difficult to carry out and also are slow. Often, they will require considerable manual handling and dexterity. Such techniques would require the person carrying out the test to take samples in a reliable manner and at exactly the right time periods. It is difficult to ensure that this is done consistently and accurately.

SUMMARY OF THE INVENTION

There are many fields in which it is desirable to monitor reactions or other changes over relatively short time frames, certainly time frames of substantially less than a second and more particularly, time frames of the order of milliseconds. For example, in the biochemical field, study of the folding kinetics of proteins is of considerable interest. Whether certain proteins are folded or unfolded effects the number of sites available for protonation, with an unfolded protein generally showing higher charge states after ESI than the same protein in a folded state. The physical basis for the observed relationship between the protein conformation in solution and the charge state distribution is still a matter of debate. Nevertheless the different charge state distributions can be used to analyze the kinetics of, for example, the folding of a protein.

Other workers in this field have recognized that developments in mass spectrometry might enable a variety of questions involving, for example, enzyme kinetics to be answered by direct observation, rather than by inferential classical enzyme kinetics (see Beyond Enzyme Kinetics: Direct Determination of Mechanisms by Stopped-Flow Mass Spectrometry by Dexter B. Northrop et al., *Bioorganic & Medicinal Chemistry*, Vol. 5, No. 4, pp. 641–644, 1997). They suggest that inhibitor dissociation constants, kinetic mechanisms of inhibition, substrate and product dissociation constants and diffusion-controlled rate constants could be determined if suitable equipment and techniques could be developed. Further, they suggest that isomerization changes, and chemical mechanisms in free energy diagrams could be determined. Strikingly, this proposal is purely theoretical, and no technique or apparatus is taught for achieving this result.

The present inventors have now realized that, by modifying an ESI apparatus, to include a mixing assembly, namely a mixing tee of novel design, the volume in which the reactants mix is decreased to reduce the time for any physical or chemical reaction to take place in the mixing region. Additionally, the inventors have further realized that the reaction time, before the mixture is vaporized and ionised can be further reduced by providing a novel electrospray outlet nozzle. These improvements enable reactants to be mixed and then passed immediately to the electrospray nozzle in a short time frame. The concentrations of the substances or reactants of interest can be measured, at an extremely short time after the reaction commences. More particularly, the present inventors propose providing a pair of capillaries connected to the ESI capillary by a capillary tee that provides almost a direct connection between the pair of capillaries and the ESI capillary. Then, the length of the capillary downstream from the tee and the flow rate for that capillary will determine the effective reaction time. This can be adjusted in accordance with the present invention, to enable measurements for different reaction times to be made.

In accordance with a first aspect of the present invention, there is provided an apparatus for determining the rate of a reaction in a liquid, the apparatus comprising: a first reactant source; a second reactant source; a junction means; first and second conduits connecting the first and second reactant sources respectively to the junction means; an ion source, for example an ESI or APCI source; and an outlet conduit connected between the junction and the ESI or APCI source, whereby reactants delivered from the first and second reactant sources mix in the junction means and pass through the outlet conduit to the ESI or APCI source, the reaction time being determined by the flow rate from the junction means to the ESI or APCI source through the outlet conduit and by the internal volume of the outlet conduit.

In accordance with another aspect of the present invention, there is provided a method of determining the rate of reaction between two reagents, the method comprising:

(1) supplying the two reagents to a junction means where the reagents mix and commence reacting;

(2) causing the reagents to pass from a junction means through an outlet conduit to an ion source, for example an electrospray or APCI source, whereby the reaction time is determined by the flow rate of the reactants and the volume of the outlet conduit to produce intermediates and products;

(3) discharging ions of the reactants, intermediates and products from the ion source;

(4) passing the ions into a mass spectrometer for analysis.

The method of the present invention can be applied to any suitable materials including biological compounds and organic and inorganic species. The invention permits measurement of the loss of reactants, identification of intermediates by their mass-to-charge ratio, or MS/MS spectrum and determination of the time course of the concentration of intermediate species, and determination of the rate of production of reaction products. As detailed below, protein folding can be studied by the different charge states that proteins in different conformations produce in ESI MS.

The invention can be used to study hydrogen/deuterium exchange of proteins in solution. Additionally, the apparatus could be heated or cooled, to study the temperature dependence of reactants of interest, and appropriate radiation can be provided to enable the study of photoactivation or light induced reactions of reagents.

BRIEF DESCRIPTION OF THE DRAWINGS

For a better understanding of the present invention and to show more clearly how it may be carried into effect, reference will now be made, by way of example, to the accompanying drawings in which.

DETAILED DESCRIPTION OF THE INVENTION

Figure 1:
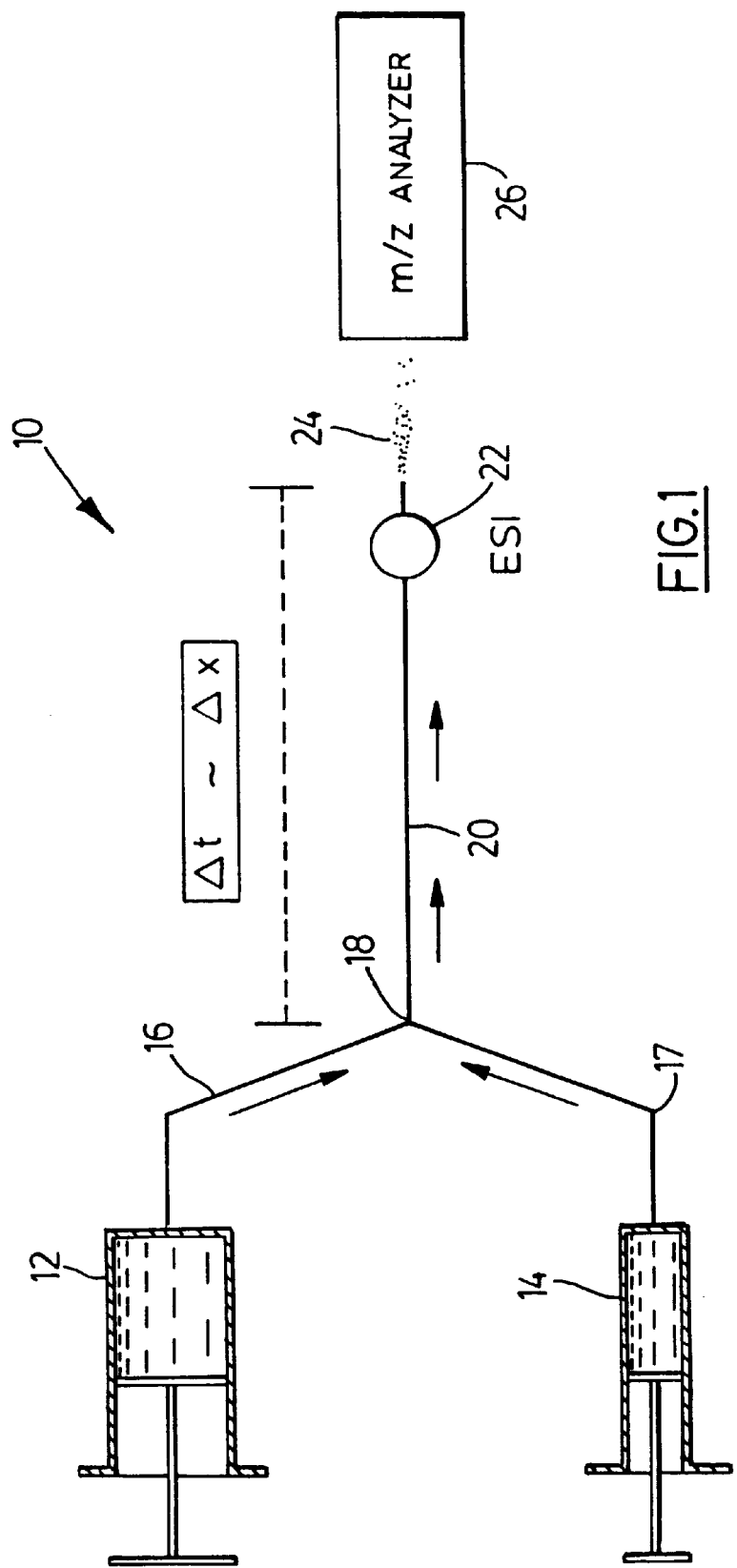
FIG. 1 is a schematic of an apparatus in accordance with a first embodiment of the present invention.

Reference will first be made to FIG. 1 which shows an apparatus in accordance with the present invention, and generally denoted by the reference 10. The apparatus 10 includes a first syringe 12 and a second syringe 14. Although syringes are shown, it will be appreciated that any suitable technique can be provided which gives a desired uniform or constant flow out from the syringe or other device, and more particularly which enables this flow rate to be regulated to provide a desired ratio of the flow rates from the two sources.

The two syringes 12, 14 are joined to a junction tee 18 by respective first and second capillary tubes or capillaries 16, 17. Each syringe is advanced by a pump (not shown) to produce a flow of liquid in the capillaries 16 and 17.

The junction tee 18 is made specifically for this apparatus whereas the other components can be a variety of conventional or proprietary equipment. The junction tee has a dead volume of approximately 3 nL.

The two capillaries 16, 17 are fused silica capillaries (TSP075150), Polymicro Technologies, Phoenix, Ariz.) and are connected by the junction tee 18 to one fused silica capillary 20. This third capillary 20 forms a reaction capillary. The three capillaries 16, 17, 20 can have the same diameters, although this is not essential.

Figure 10:
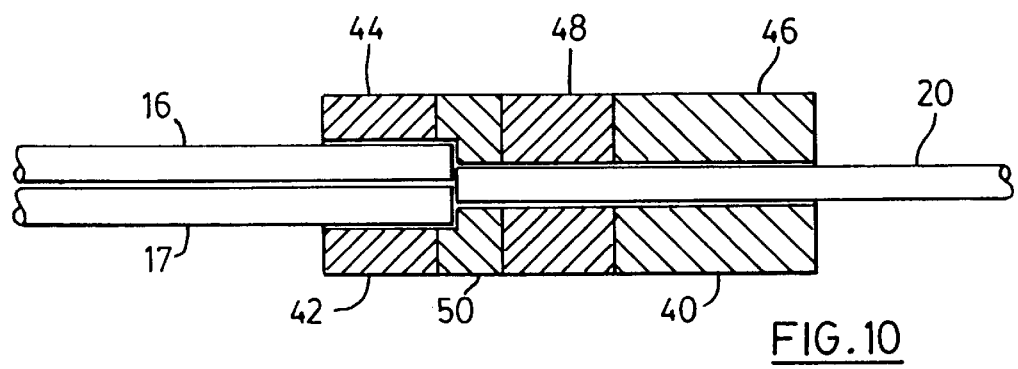
FIG. 10 is a schematic on a large scale showing a mixing tee as incorporated in the first and second embodiments of the apparatus.

A schematic cross-section through the junction tee 18 is given in FIG. 10, from which it can be seen that the tee 18 does not have a "T" shape, but rather has all the capillaries 16, 17, and 20 parallel to one another. While this preferred embodiment has all the capillaries parallel to one another, any arrangement providing a small dead volume at the junction could be used.

The junction tee 18 is made out of a 10 mm long piece of Flexon HP tubing 40 (1/16" OD×0.007" ID; supplied by Alltech, Deerfield Ill.). In one end 42 the hole in the tubing is slightly widened by a sharp needle so that it can just accommodate two parallel fused silica capillaries. This hole should be approximately 2 mm deep. Both capillaries are pushed into the hole as far as possible. Then the opening of the Flexon tubing is sealed by melting the plastic with a hot soldering iron, as indicated by the hatching at 44. Now the reaction capillary 20 is pushed through the remaining hole in the other side end 46 of the Flexon tubing 40 until it is in contact with the two other capillaries 16, 17, but sufficiently spaced to provide a fluid connection. The capillaries 16, 17 have an internal diameter of 75 microns and an external diameter of 150 microns. Now the other end 46 of the Flexon tubing is sealed by applying heat as indicated at 48. Care has to be taken that the molten plastic does not clog the adjacent or abutting capillary ends inside the Flexon tubing and hence an unmelted zone is left at 50. Afterwards the mixing tee is visually inspected by means of a stereomicroscope (magnification about 40 times) to ensure that the mixing volume is as small as possible. The mixing volume of properly assembled tees is typically in the range of roughly 3 nL. It will be appreciated that the dimensions given above are just an example and depend on the specific requirements for different applications.

The third outlet or reaction capillary 20 is connected to an electrospray (ESI) or APCI source 22, which as indicated would generate an ion stream 24 which passes to an analyzer 26. It would be understood that the appropriate voltage would be applied to the ESI source in known manner.

As indicated, the third capillary 20 defines a length of $\Delta x$ between the mixing point and the outlet of the ESI source 22. This length $\Delta x$ and the flow velocity through the capillary 22 control the reaction time.

As an example, the apparatus of FIG. 1 was used to study the folding kinetics of proteins. Different protein conformations in solution are monitored by the different charge state distributions that they produce during ESI. The time resolution is in the range of ca. 0.1 s. The feasibility of this new technique is demonstrated by measuring the refolding kinetics of acid-denatured cyt c. The fact that at low ionic strength this protein has five pH-dependent conformational states labelled I–V is well-established. The reversible "acid transition" II–III has an apparent pK of roughly 2.5 and leads from a largely unfolded conformation (II) to the native state (III). In this first example, the apparatus of FIG. 1 is used to study the kinetics of the refolding from state II to state III.

Horse heart cyt c, purchased from Sigma (St. Louis, Mo.), was used without further purification. HPLC grade glacial acetic acid and hydrochloric acid were obtained from Fisher Scientific (Nepean, Canada), and $N(CH_3)_4Cl$ was from Aldrich (Milwaukee, Wis.).

Two syringes 12, 14 were advanced simultaneously by a syringe pump (model 22, Harvard Apparatus, South Natick, Mass.) at a total flow rate of 33 $\mu$L/min. Syringe 12 (volume of 1 mL, flow of 30 $\mu$L/min) contained $5\times10^{-4}$ M $N(CH_3)_4Cl$ in water; syringe 14 (volume of 0.1 mL, flow of 3 $\mu$L/min) contained cyt c ($1\times10^{-5}$ M) at pH 2.4 in a 5% solution (v/v) of acetic acid in water. The pH of each solution was measured with a calibrated accumet pH electrode (model 15, Fisher Scientific). The syringes 12, 14 are connected to respective fused silica capillaries 16, 17 (TSP075150, i.d. of 75±3 $\mu$m, Polymicro Technologies, Phoenix, Ariz.) by a connector (P742, Upchurch Scientific, Oak Harbor, Wash.). These two capillaries 16, 17 are connected to third "reaction" capillary 20, which has the same internal diameter as the other two capillaries, by the tee 18. The dead volume of the tee 18, approximately 3 nL, corresponds to a calculated mixing time of roughly 5 ms for the flow rates given above.

Refolding of the protein is initiated upon mixing the liquids from the two syringes in the tee. The reaction time is controlled by the length of the reaction capillary 20 between the mixing point and the electrospray source 22. A distance of 1 cm in the capillary corresponds to a time of 81±6 ms. For this study, reaction capillaries between 1.2 and 186 cm long were used, corresponding to times between 0.1±0.007 and 15.5±1.1 s, respectfully. The uncertainties in the times are due to the manufacturers' stated uncertainties in the capillary diameters. In order to accommodate the shortest reaction capillaries, an ESI sprayer was designed which had a stainless steel spray capillary (i.d.=200 $\mu$m) with an overall length of only 7 mm. The high voltage for the sprayer was applied to this capillary.

Protonated gas phase protein ions were formed at the exit of the reaction capillary by pneumatically assisted electrospray and analyzed in a custom quadrupole mass spectrometer system which is similar to that described in *Int. J. Mass Spectrom. Ion Proc.* 162, 121–127, 1997. The quadrupole had a field radius that was smaller than for most commercial instruments and the frequency of the quadrupole power supply was lower, to enable the detection of ions with a higher mass to charge ratio (up to 11,000). However, these experiments could have been performed on any other quadrupole mass spectrometer system, and the modifications included in this system were not essential. The ions were passed through a dry nitrogen "curtain" gas and then a 0.25 mm diameter sampling orifice directly into an RF only quadrupole, and from there through a short RF prefilter and to the mass-analyzing quadrupole. Fluctuations in the sensitivity of the instrument were compensated for by using $N(CH_3)_4^+$ ions as an internal standard in known manner. The presence of this internal standard at $5\times10^{-4}$ M did not have any noticeable effects on the mass spectra of cyt c at pH 2.4 or 3.0. As the use of an internal standard is not always a necessary method for dealing with sensitivity fluctuations, the second study (unfolding of hMb, FIGS. 4, 5) was carried out without using internal standard. All measurements were carried out at room temperature (21±1° C.).

Figure 2:
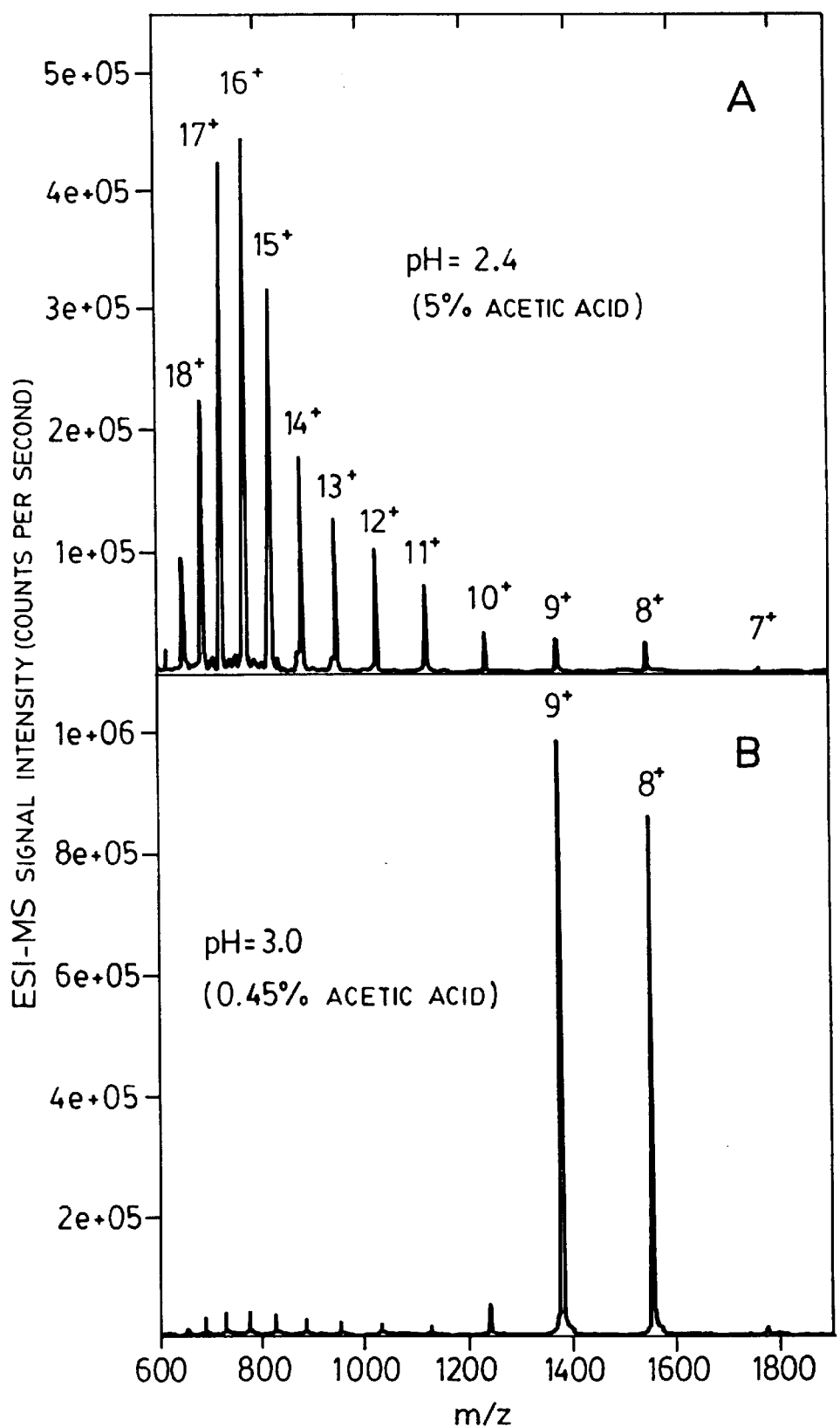
FIG. 2 is a graph showing ESI mass spectra of cytochrome c, in mixtures of acetic acid and water at different pH.

Reference will now be made to FIG. 2 which shows the ESI mass spectra for cyt c in aqueous solutions of 5 and 0.45% acetic acid (v/v), corresponding to pH 2.4 and 3.0, respectively. At pH 2.4 (FIG. 2A), cyt c is predominantly in the largely unfolded state II and shows a rather broad charge distribution with (cyt c+16H$^+$)$^{16+}$ being the most intense peak. At a pH of 3.0 (FIG. 2B), the conformational equilibrium is shifted toward the native state III. The mass spectrum now shows a rather narrow distribution of charge states which consists almost entirely of the 8$^+$ and 9$^+$ peaks. The relative contribution of higher charge states is about 10% and suggests that at this pH some of the protein remains in state II. These pH-dependent changes in the mass spectrum are fully reversible, although the data are not shown. It was found that the exact shapes of the spectra in FIG. 2 depend on experimental details like the position of the sprayer.

Figure 3:
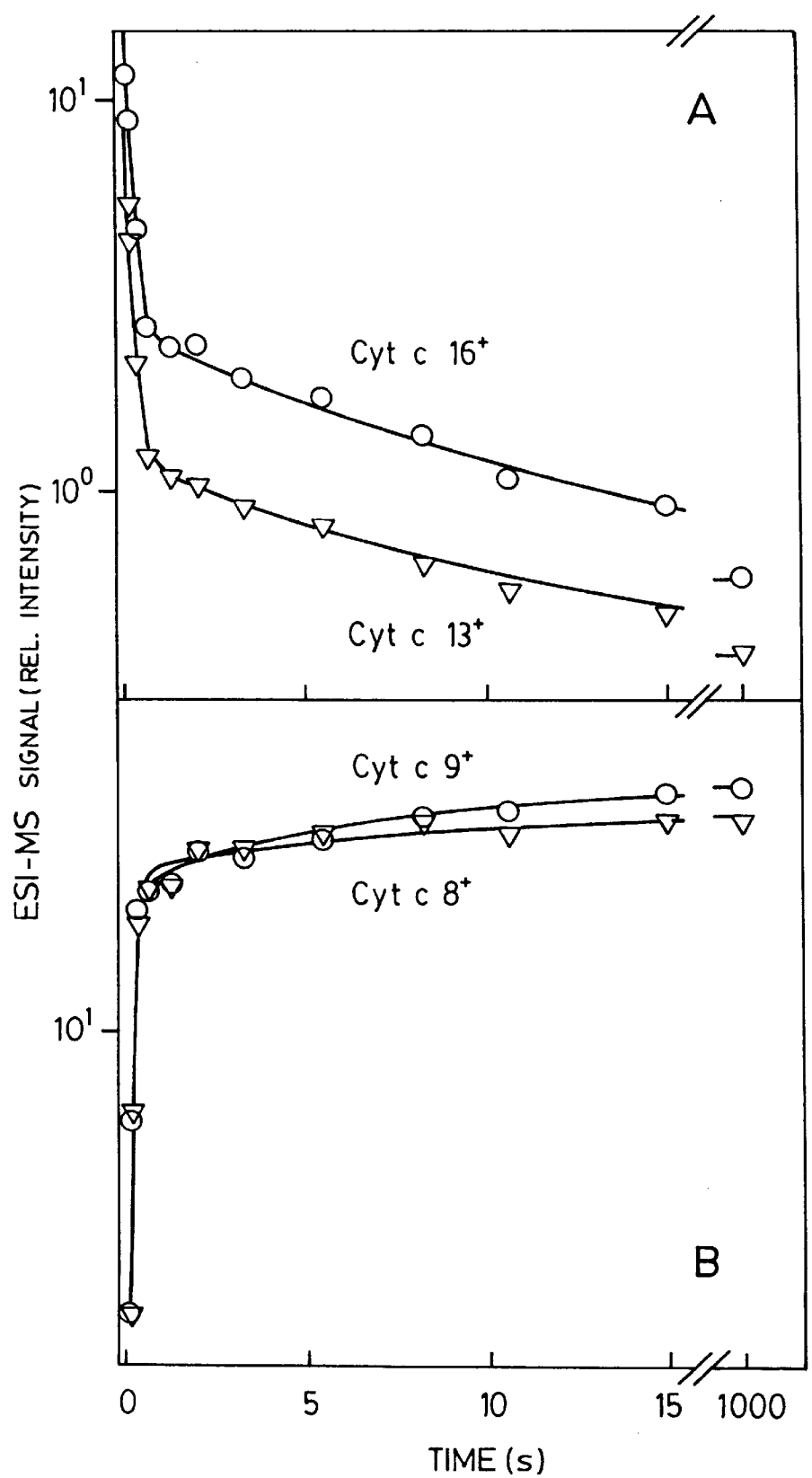
FIG. 3 is a graph showing the time course of signal intensity in the mass spectrum of cyt c for different charge states.

The refolding of cyt c following a pH jump from 2.4 to 3.0 was monitored for the charge states 8$^+$–19$^+$ by measuring the intensity of each charge state as a function of time (time-resolved ESI MS). Measurements were made from 0.1 to 15.5 s after mixing the solutions for the two syringes. This was achieved by maintaining a constant flow rate from the syringes and altering the length of the capillary tube 20. Intensities for completion of the folding reaction were taken from the stationary mass spectrum of cyt c at pH 3.0. The intensities for each peak in the spectrum were normalized to the intensity of the internal standard. The data used for this study represent the average of three independent sets of experiments. The normalized intensities of cyt c peaks $10^+$–$19^+$ decrease and the intensities of peaks $8^+$ and $9^+$ increase with time, reflecting the decay of the unfolded and formation of the folded state, respectively. Some typical data are depicted in FIGS. 3a, 3b.

These Figures show the time course of the normalized signal intensity in the mass spectrum of cyt c for charge states $13^+$ and $16^+$ (A) and $8^+$ and $9^+$ (B). Intensities were measured at different times after changing the pH in the solution from 2.4 to 3.0. The first data point in each curve represents t=0.1 s; the last one ("t=1000 s") is taken from the stationary mass spectrum measured at pH 3.0. Solid lines are fits to the experimental data. The ordinates in this figure have a logarithmic scale.

The method of the present invention has also been applied to the study of acid-induced denaturation of holo-myoglobin (hMb) following a pH-jump from 6.5 to 3.2. As detailed below, the different protein confirmations were detected by different charge state distributions generated during ESI.

Figure 4:
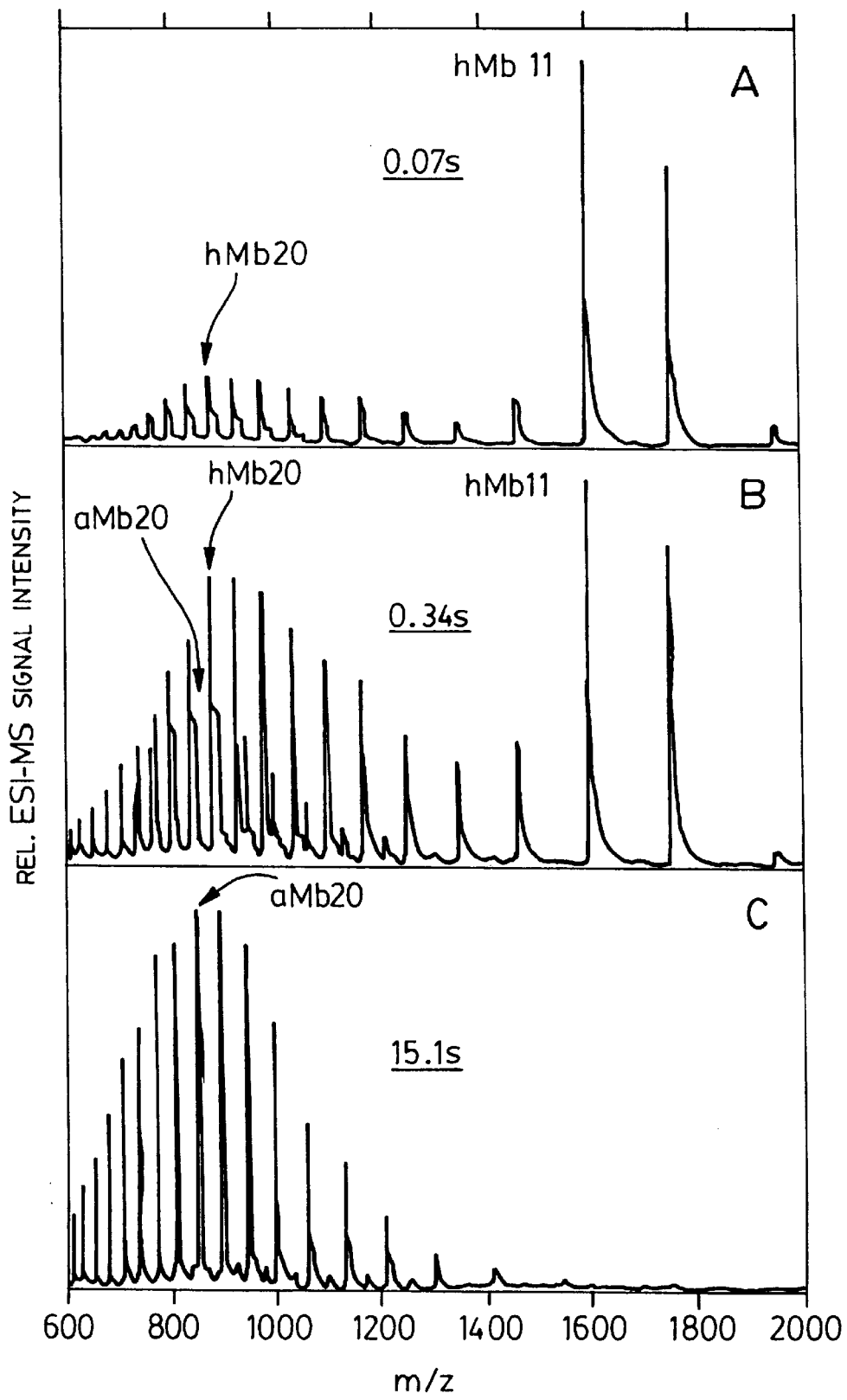
FIG. 4 is a graph of ESI mass spectra of myoglobin at different times after a pH jump.
Figure 5:
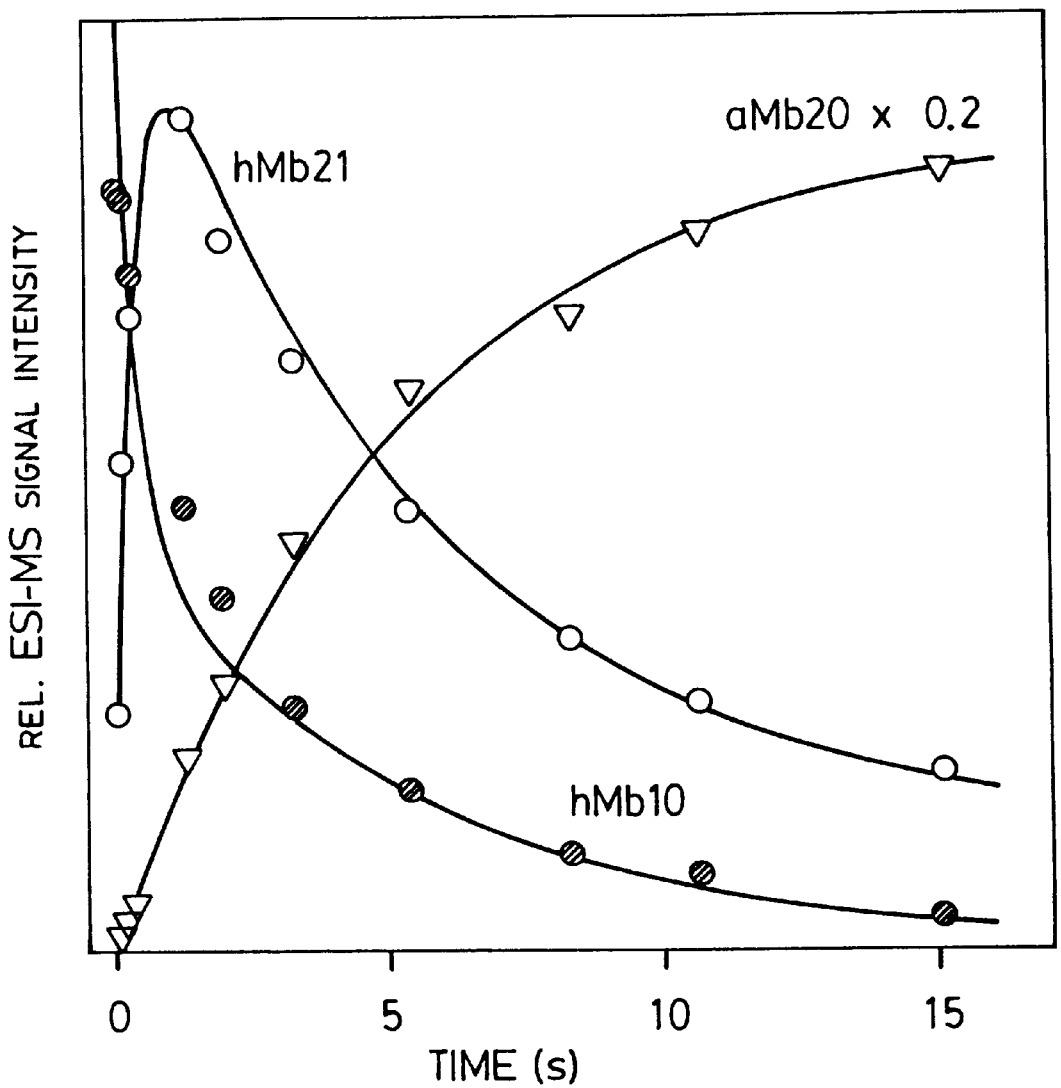
FIG. 5 is a graph showing the time course of the signal intensity for three peaks in the ESI mass spectrum of myoglobin after the pH jump.

Reference will now be made to FIGS. 4 and 5, which show application of the present invention to acid-induced denaturation of myoglobin. This technique was carried out substantially as described above. Here, the two syringes 12, 14 had the same volume, with each having a total volume of 1 mL.

Figure 7:
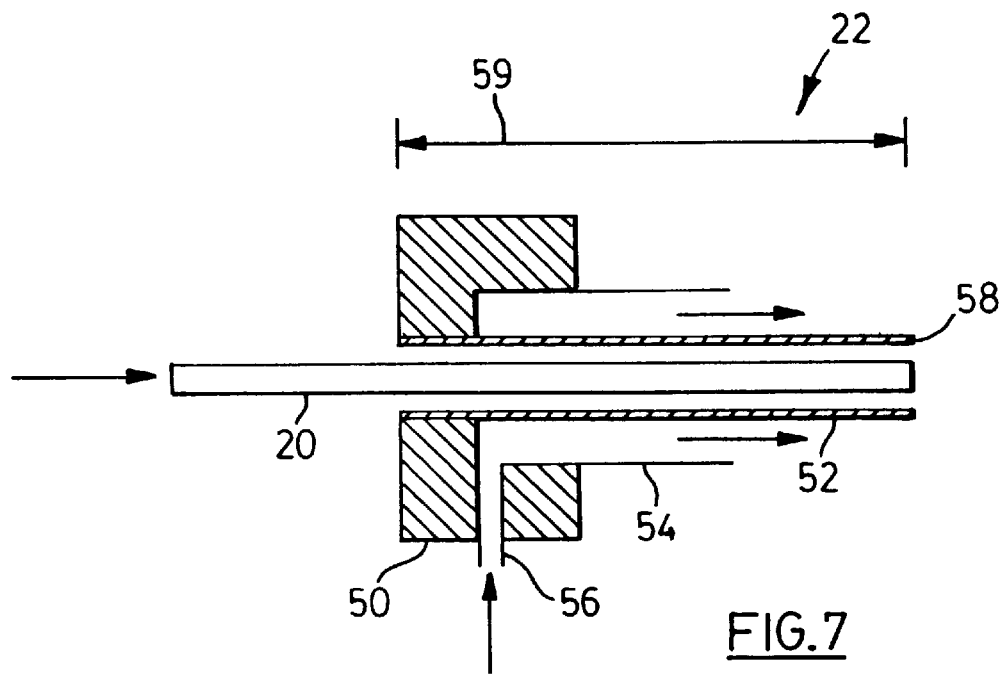
FIG. 7 is a schematic cross sectional view through an electrospray source.

The two syringes 12, 14 of FIG. 1 were simultaneously advanced by a syringe pump. One syringe contained 40 $\mu$M hMb in water (pH 6.5), and the other contained a 0.45% solution (v/v) of acetic acid in water. The experiments were performed without using an internal standard, and this experiment shows that an internal standard is not necessary for the present invention. Initiation of hMb denaturation was triggered by mixing the liquids from both syringes in the tee 18, to produce a final pH of 3.2. The tee 18 was connected to the ESI source 22 by the reaction capillary 20 with an inner diameter of 75 $\mu$m. As before, the reaction time was controlled by the length of this reaction capillary. Capillary lengths varied between 0.9 and 186 cm corresponding to reaction times between 0.07 and 15.1 s, respectively. The total flow rate was kept constant throughout the experiment at 33 $\mu$L/min. Multiply charged gas phase proteins were generated by pneumatically assisted ESI, for example as shown in FIG. 7, and were analyzed by a custom quadrupole mass spectrometer system, as detailed above. Depending on the voltage settings in the ion sampling interface of the mass spectrometer, the heme-protein interactions in hMb can be disrupted by collisionally activated dissociation. For this work, the voltage difference between the orifice and the RF-only quadrupole was +26 V. Under these conditions, no dissociation of the heme-protein complex was observed when electrosprayed under native conditions. A further decrease in this voltage difference was found to result in a pronounced "tailing" of the observed peaks on the high mass side that was probably caused by inefficient desolvation of the ions. Experiments were carried out at room temperature (21±2° C.).

The ESI mass spectra of myoglobin recorded at different times after a pH-jump from 6.5 to 3.2 are shown in FIG. 4. The spectrum obtained after 70 ms (FIG. 4A) exhibits a bimodal distribution of hMb charge states with a primary maximum at hMb11 (hMb+11H$^+$)$^{11+}$, and a secondary maximum around hMb20. These two groups of peaks are attributed to populations of hMb having a native-like and a more unfolded conformation in solution, respectively. Closer inspection reveals the presence of some minor apomyoglobin (aMb, holomyoglobin which has lost its heme group) peaks in the spectrum. After 0.34 s (FIG. 4B), the relative contribution of hMb in high charge states is drastically increased and that of the low hMb charge states has decreased, indicating that more of the hMb has adopted the unfolded conformation in solution. Also, in FIG. 4B the contribution of aMb peaks in the spectrum has increased over that of FIG. 4A. The charge state distribution of the aMb peaks is centered at around aMb20 which indicates that the aproprotein is also in an unfolded conformation. The aMb peaks dominate the spectrum recorded after 15.1 s (FIG. 4C); those of hMb have a total contribution of <5%. The spectrum depicted in FIG. 4C is similar to the stationary spectrum of Mb recorded at pH 3.2, but the latter shows an even smaller contribution from hMb peaks (data not shown). Under the experimental conditions used in this study, the dissociated heme appears as a weak peak at m/z=615 (heme$^{1+}$). The data shown in FIG. 4 demonstrate that after a pH-jump from 6.5 to 3.2, the native protein is eventually transformed into an unfolded form with strongly diminished heme-protein interactions. During this process, a transient intermediate is formed which is considerably unfolded but still binds the heme with sufficient strength to prevent the dissociation of the complex during ESI.

To analyze the kinetics of this process further, the intensities of individual hMb and aMb peaks in the ESI mass spectrum were monitored as a function of time. Measurements were made from 70 ms to 15.1 s after the pH-jump. Typical data are shown in FIG. 5 and represent the average of four sets of experiments. Solid lines are the result of a global fitting procedure. Low charge states of the holo-protein, e.g., hMb10, decay rapidly. Concurrently, an increase in the intensity of more highly charged hMb peaks is observed on the same time scale, as exemplified by hMb21. The latter peaks reach maximum intensity after about 1 s and reflect the formation of unfolded hMb as a kinetic intermediate. Subsequently, these peaks decay considerably more slowly. This much slower process is accompanied by an increase of highly charged aMb peaks (for example, aMb20 in FIG. 5).

Thus, both of these two sets of experiments show that reactions that happen within relatively short time frames, e.g. of the order of seconds or fractions of seconds can readily be analyzed using the apparatus of the present invention. It is a simple matter to change the length of the third capillary to achieve a different reaction time.

Alternatively, the reaction time can be changed by changing the flow rate through the capillary 20, which can then be of constant or fixed length. It is also possible to change both the capillary length and the flow rate, to give a desired reaction time.

The technique does not require parallel capillaries in the junction tee. Any other mixing device with a suitable dead volume could be used. The technique can be used to identify intermediates by their mass or MS/MS spectrum, such as unfolded hMb to determine the time course of the concentration of intermediate species, and to determine the rate of production of reaction products (as illustrated by aMb).

Figure 6:
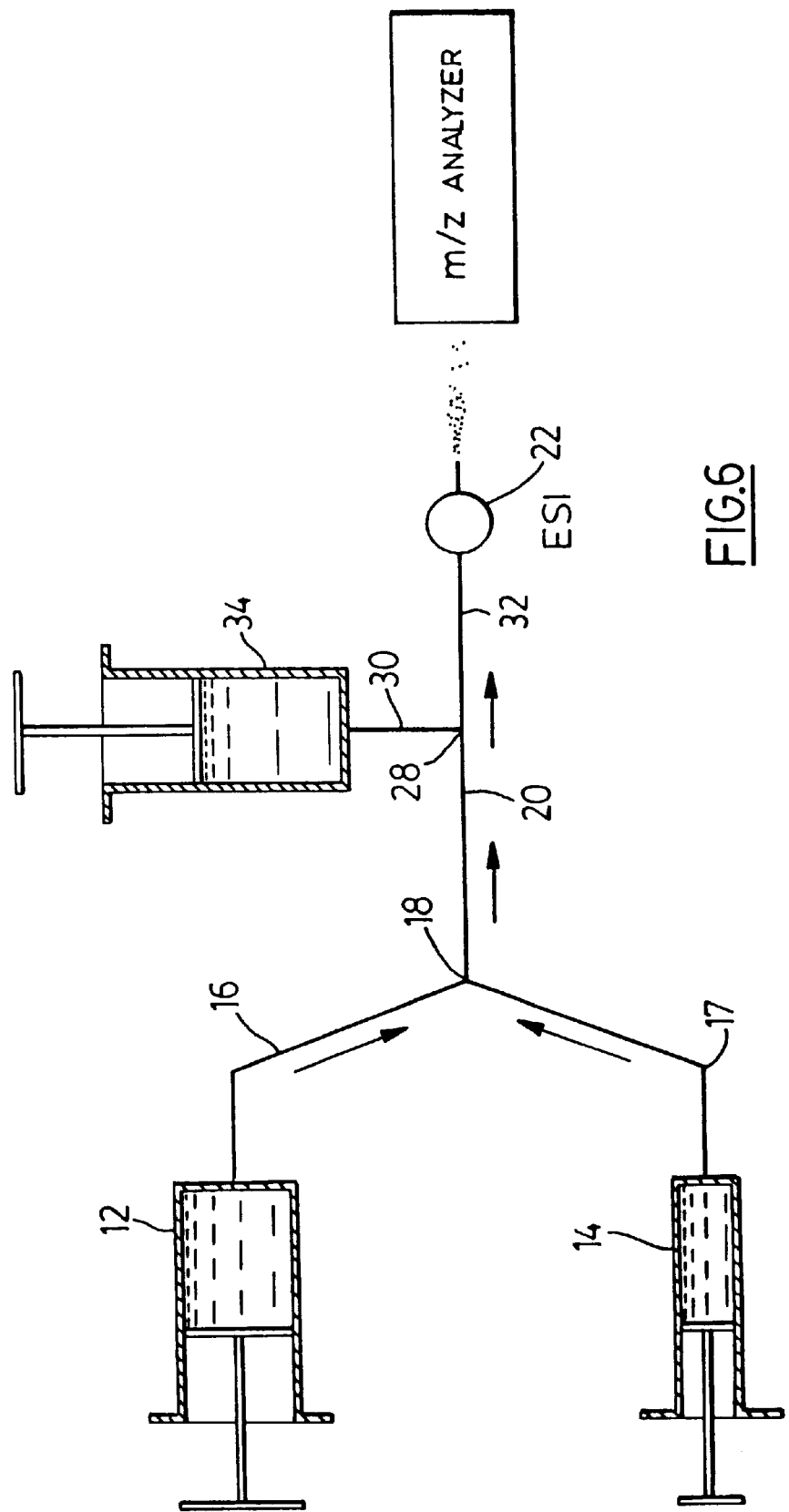
FIG. 6 is a schematic of an apparatus in accordance with a second embodiment of the present invention.

Referring to FIG. 6, this shows a further embodiment. Here, in addition to the capillary 20, a further tee junction or connection 28 is provided, which has as input connections the capillary 20 and an additional input capillary 30. The junction 28 is connected to an additional output capillary 32. Here, an additional reactant is introduced through the additional input capillary 30 from a syringe or other source 34 and mixed with the reagents that are already reacting, which pass from the capillary 20 into the secondary tee junction 28. A further reaction then takes place in the output capillary 32, before being connected to the ESI source 22. This technique can be used to explore more complex reactions. Moreover, where there are difficulties with the stability of reaction products, this technique can be used to stabilize products of a reaction occurring in the capillary 20, before they are passed to the ESI or other source 22.

The analysis of hydrogen/deuterium exchange in proteins in solution is often of interest. The technique of changing the reaction time by changing the flow rate could have a particular applicability to the study of hydrogen/deuterium exchange in proteins in solution.

Reference will now be made to FIG. 7 which shows in detail the electrospray source 22. A brass mounting 50 includes a bore in which a stainless steel capillary 52 is mounted. This capillary 52 has an internal diameter of 200 microns and the outlet capillary 20 slides into it. The block 50 also provides on one side an enlarged bore into which a tube 54 is fitted, coaxially surrounding the stainless steel capillary 52. This defines an annulus for an air flow, and an air inlet 56 in the block 50 opens into this annulus.

The end of the capillary 20 is flush with the end of the stainless steel tube 52, as indicated at 58, and this provides the actual electrospray outlet. The tube 52 is electrically connected to the block 50, and the block 50 is in turn connected to the desired potential source. As indicated at 59, the overall length of the electrospray source, including the brass mounting element 50, to the outlet 58 is just 7 mm. This is considerably shorter than the dimension of around 5 cm, commonly available in commercial instruments. This considerably reduces the time for solutions to flow through the source and obtains maximum benefit from the minimized volume in the junction tee 18.

Figure 8:
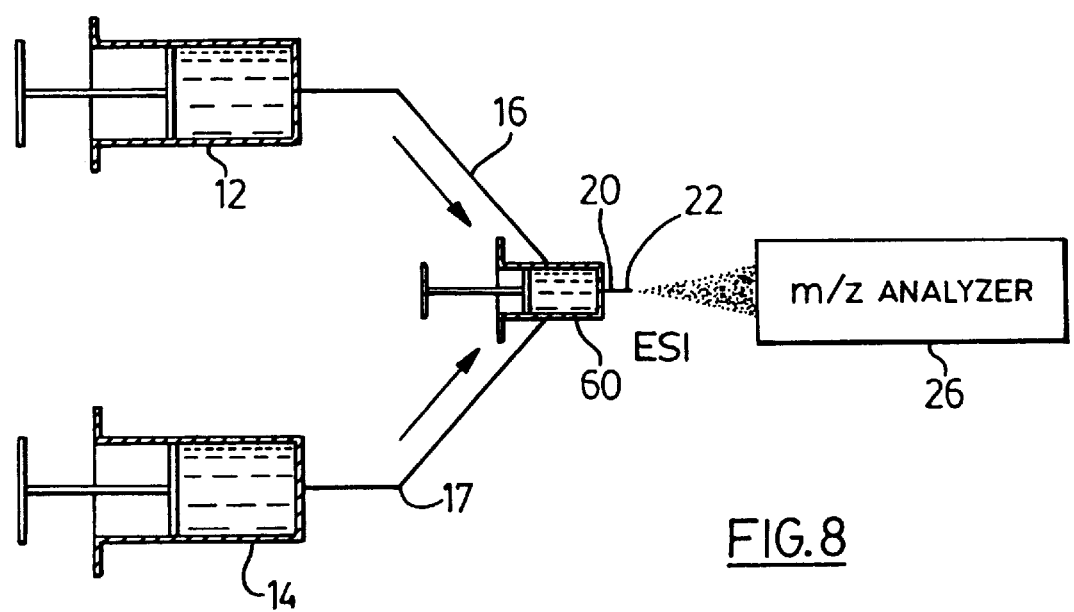
FIG. 8 is a schematic of an apparatus in accordance with a third embodiment of the present invention.

Reference will now be made to FIG. 8, which shows the third embodiment of the present invention, and in which, for simplicity and brevity, like parts are given the same reference numeral as in earlier embodiments. The description of these common or like components is not repeated.

Essentially, in FIG. 8, the mixing tee 18 is replaced by a reaction chamber 60, here indicate by a syringe. This reaction chamber would typically have an internal volume in the range 0.01 to 10 mL.

In use, a reaction is initiated by discharging the contents of the two syringes 12, 14, through the capillaries 16, 17 into the syringe 60, which is allowed to expand to accommodate the incoming reactants. This mixing can occur in a time as short as 1 millisecond, when the plungers of the syringes 12, 14 are moved fast enough, e.g. by applying pneumatic pressure. Alternatively, any suitable kind of pump or other delivery device could be used, to supply the reactant liquids to the syringe 60.

After the reaction cell or syringe 60 is filled and the reaction has been allowed to continue for a set time, the contents of the syringe 60 are discharged through the electrospray source 22, by displacing the piston of the syringe 60. Again, this can be achieved by pneumatic pressure or other powered devices.

As for other embodiments, the capillary 22 can be made very short, e.g. 1 millimeter. For ESI, the capillary forming the source 22 is formed from stainless steel and the necessary high voltage is applied directly to this.

As before, a mass spectrometer or analyzer is provided to record the whole spectra for different reaction times. It would be desirable to use Time of Flight (TOF) mass spectrometer for this purpose, as this can record spectra in as little as 100 microseconds or less. Mass spectrometers which are not capable of performing these rapid measurements could be used to monitor the intensity of a few ions as a function of time. Here, the length of the reaction time is determined by the holding time in the syringe 60 so that it is not necessary to change the length of the outlet capillary 20. Rather, the outlet capillary 20 should be as short as possible, so that once discharge from the syringe or reaction chamber 60 is commenced, there is little delay before the liquid is ionized.

Depending upon the particular application, other elements can be added to the apparatus in FIG. 8. For example, valves could be provided between the syringes 12, 14 and the reaction cell 60, for closing off the capillaries 16, 17 after the reaction cell has been filled; this ensures that during discharge of the syringe 60, there is no back flow into the capillaries 16, 17. The reaction cell or syringe 60 could be provided with one or more additional inlet or outlet valves, to remove excess liquid and to allow rinsing of the cell before commencing a new test, and also to remove air bubbles from the system. Further, it may be desirable to provide a mixing cell to ensure intimate mixing of the reactant liquids immediately prior to their entry into the cell or syringe 60. This would ensure a well-defined start to the reaction, but would require the mixing cell to be closely coupled to the syringe 60, to avoid additional dead time.

Figure 9:
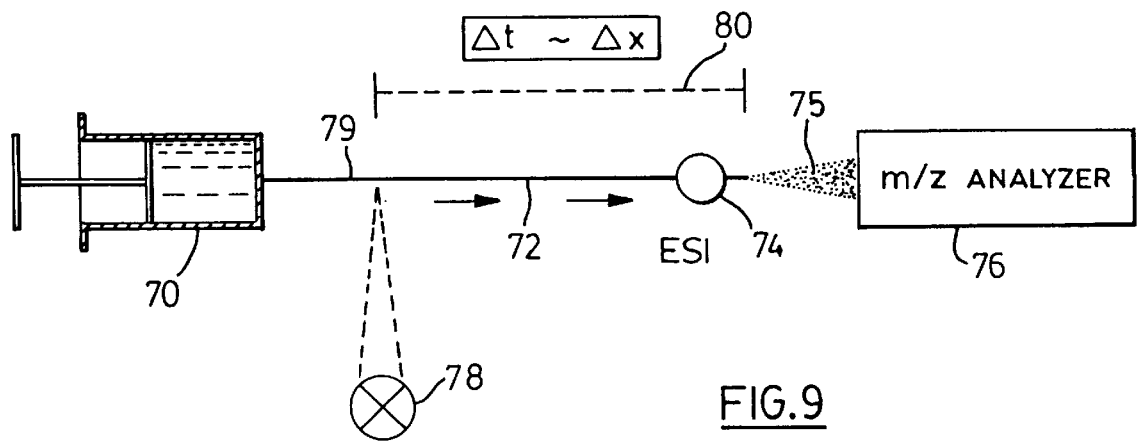
FIG. 9 is a schematic of an apparatus in accordance with a fourth embodiment of the present invention.

Reference will now be made to FIG. 9, which shows a fourth embodiment of the present invention. Here, a syringe or other source 70 is connected to a capillary 72, which in turn is connected to an ESI or other source 74, which is the source shown in FIG. 7. Ions 75 generated by the source 74 are detected in an analyzer 76. A light source 78 illuminates the capillary 72. As indicated at 80, this gives a length $\Delta x$, between the point of illumination and the outlet of the source 74, during which a reaction can occur.

The apparatus of FIG. 9 is intended to enable study of the kinetics of a light-induced reaction. This can be done in various ways. For example., as shown in FIG. 9, a specific portion 79 of the capillary could be illuminated and the length adjusted to give a desired lumination time and the distance $\Delta x$ would then determine the time after illumination until the ions are generated. Alternatively, the light source 78 can be caused to travel along the capillary 72 at the same velocity as the liquid is flowing so that a certain portion of liquid would be subject to illumination for a known time. The light source 78 can be provided with known optical means to control the area of illumination, e.g. by way of lens, a small diameter pin hole aperture and the like.

As shown in FIG. 9, for the study of change in a single chemical, which may be a physical or chemical change, just one syringe 70 is required. It will be appreciated that this technique is equally applicable to reactions, of any sort, involving two or more liquids. Thus, the concept of photoactivation could be added to one or more of the capillaries shown in the other embodiments of the present invention.

Additionally, it will be appreciated that other inputs can be provided, to study their effects on reaction rates. For example, the apparatus, or at least the capillary tube 20, can be heated or cooled to study the temperature dependence of reactions and may also be used with photoactivation of reagents. It is envisaged that the apparatus could be used to study physical changes in a single reactant.

We claim:

1. An apparatus for determining the rate of a reaction in a liquid, the apparatus comprising: a first reactant source; a second reactant source; a junction means; first and second conduits connecting the first and second reactant sources respectively to the junction means; an ion source; and an outlet conduit connected between the junction and the ion source, whereby reactants delivered from the first and second reactant sources mix in the junction means and pass through the outlet conduit to the ion source, the reaction time being determined by the flow rate from the junction means to the ion source through the outlet conduit and by the internal volume of the outlet conduit.

2. An apparatus as claimed in claim 1, wherein the outlet conduit comprises an outlet capillary tube and the junction means comprises a junction tee.

3. An apparatus as claimed in claim 2, wherein the first and second conduits comprise first and second capillary tubes, and wherein the junction tee comprises a general tubular member enclosing ends of the first, second and outlet capillary tubes, wherein the ends of the first, second and outlet capillary tubes are substantially parallel to one another and the end of the outlet tube is adjacent ends of the first and second capillary tubes, to provide minimal internal volume in the junction tee.

4. An apparatus as claimed in claim 3, wherein the junction tee has a volume of less than 3 nL.

5. An apparatus as claimed in claim 1, wherein the junction means comprises a container having a volume of 0.01 to 10 milliliters, and wherein the outlet conduit means has an internal diameter of around 10 to 100 microns and a length of 1 millimeter.

6. An apparatus as claimed in claim 5, wherein the junction means comprises a variable volume chamber including means for varying the volume of the variable volume chamber to displace liquid therefrom, whereby the volume of the variable volume chamber can be increased to fill the chamber with the reactants to commence a reaction and said means for varying the volume is used to discharge the reactants through the outlet conduit.

7. An apparatus as claimed in claim 1 or 5, wherein the ion source comprises one of an ESI source and an APCI source.

8. A method of determining the rate of reaction between two reagents, the method comprising:

(1) supplying the two reagents to a junction means where the reagents mix and commence reacting;

(2) causing the reagents to pass from a junction means through an outlet conduit to an ion source, whereby the reaction time is determined by the flow rate of the reactants and the volume of the outlet conduit to produce intermediates and products;

(3) discharging ions of the reactants, intermediates and products from the ion source;

(4) passing the ions into a mass spectrometer for analysis.

9. A method as claimed in claim 8, wherein the reaction time is varied by varying the length of the third conduit.

10. A method as claimed in claim 8, wherein the reaction time is varied by varying the flow rate of the reactants.

11. A method as claimed in claim 8, wherein the reaction time is varied by varying both the flow rate of the reactants and the length of the outlet conduit.

12. A method as claimed in claim 8, which includes providing a container having a significant volume, relative to the volume of the outlet conduit, in step (1) first supplying the reactants to the container, to mix the reactants, and subsequently passing the reactants from the container to the outlet conduit.

13. A method as claimed in claim 12, which includes passing the reactants through a mixing cell, to ensure mixing of the reactants, before passing the reactants to the container.

14. A method as claimed in claim 13, which included providing valves to control flow to and from the container and operating the valves to control flow of reactants to the container and flow of reactants, intermediates and products form the container.

15. A method as claimed in claim 8 or 12, which includes generating ions by one of an ESI source and an APCI source.

16. A method of determining the rate of a reaction, the method comprising:

(1) delivering at least one liquid reactant to a conduit having a known internal volume;

(2) subjecting the liquid reactant to at least one of a physical change and a chemical change as it passes through the outlet conduit;

(3) passing the liquid reactant from the outlet conduit through an ion source outlet, to generate a stream of ions;

(4) passing the ions into a mass spectrometer to determine the mass spectrum of the reactant, and determining the reaction time in the outlet conduit.

17. A method as claimed in claim 16, which includes in step (2) subjecting the liquid reactant to a light-induced reaction.

18. A method as claimed in claim 17, wherein ions are generated by one of an ESI source and an APCI source at atmospheric pressure.

19. A method as claimed in claim 16, wherein ions are generated by one of an ESI source and an APCI source at atmospheric pressure.

* * * * *